United States Patent [19]

Rinehart, Jr.

[11] Patent Number: 4,737,510

[45] Date of Patent: Apr. 12, 1988

[54] **BIOACTIVE METABOLITES FROM THE CARIBBEAN SPONGE *AGELAS CONIFERIN***

[75] Inventor: Kenneth L. Rinehart, Jr., Urbana, Ill.

[73] Assignee: The Board of Trustees of The University of Illinois, Urbana, Ill.

[21] Appl. No.: 913,819

[22] Filed: Sep. 30, 1986

[51] Int. Cl.[4] .................. C07D 403/30; C07D 233/30; C07D 473/00; A61K 31/415

[52] U.S. Cl. .................................. 514/388; 548/316; 548/309; 548/303; 548/327; 548/301; 514/392; 514/389; 106/287.21

[58] Field of Search ............... 548/316, 309, 303, 327, 548/301; 514/392, 389, 388

[56] References Cited

U.S. PATENT DOCUMENTS

4,370,484  1/1983  Faulkner ........................... 548/316

OTHER PUBLICATIONS

Nakamura, H. et al. (1984), "Agelasine-A, -B, -C and -D, Novel Bicyclic Diterpenoids with a 9-Methyladeninium Unit Possessing Inhibitory Effects on Na, K-Atpase from the Okinawan Sea Sponge Agelas sp.", Tetrahedron Lett., 25(28):2989-2992.

Wu, H. et al. (1984), "Agelasine-E and -F, Novel Monocyclic Diterpenoids with a 9-Methyladeninium Unit Possessing Inhibitory Effects on Na, K-Atrase Isolated from the Okinawan Sea Sponge, *Agelas Nakamurai* Hoshino", Tetrahedron Lett., 25(34):3719-3722.

Nakamura, H. et al. (1983), "Agelasidine-A, A Novel Sesquiterpene Possessing Antispasmodic Activity from the Okinawa Sea Sponge *Agelas* sp.", Tetrahedron Lett., 24(38):4105-4108.

Cullen, E. and Devlin J. P. (1975), "Agelasine: A Novel Quaternary 9-Methyladenine from the Sponge *Agelas dispar*", Can. J. Chem. 53:1690-1691.

Nakatsu, T. et al. (1984), "Structure of the Diterpene Portion of A Novel Base from the Sponge *Agelas mauritiana*", Tetrahedron Lett., 25(9):935-938.

Capon, R. J. and Faulkner, D. J. (1984), "Antimicrobial Metabolites from a Pacific Sponge, Agelas sp.", J. Am. Chem-Soc., 106:1819-1822.

Kanazawa, A. et al. (1979), "Sterols of the Sponges (Porifera, Class Demospongiae)", Comp. Biochem. Physiol., 62B:521-525.

DiGiacomo, G. et al. (1983), "Sterols from the Sponge *Agelas oroides*", Comp. Biochem. Physiol., 74B:499-501.

Bohlin, L. et al. (1980), "Minor and Trace Sterols in Marine Invertebrates XVI.", Steroids, 35(3):295-304.

Walker, R. P. et al. (1981), "Sceptrin, an Antimicrobial Agent from the Sponge *Agelas sceptrum*", J. Am. Chem. Soc., 103:6772-6773.

Faulkner, D. J. (1983), "Sceptrin an antimicrobial agent from *Agelas sceptrum*", Chem. Abstr., 98:155209x.

Buchecker, R. et al. (1977), "Carotenoids from Marine Sponges (Porifera): Isolation and Structure of the Seven Main Carotenoids from *Agelas schmidtii*", Helv. Chim. Acta 60(8) #273:2780-2788.

Chevolot, L. et al. (1977), "Isolation of 1-Methyl-4,-5-Dibromopyrrole-2-Carboxylic Acid and Its 3'-(-Hydantoyl)Propylamide (Midpacamide) from a Marine Sponge", Heterocycles 7:891-894.

Chevolot, L. "Guanidine Derivatives" in Marine Natural Products, Chemical and Biological Perspectives, Scheurer; P. L., ed., Academic Press, NY, 1981, vol. 4, pp. 54-91.

Nakamura, H. et al., "Keramadine, a Novel Antagonist of Serotonergic Receptors Isolated from the Okinawan Sea Sponge *Agelas* sp." (1984), Tetrahedron Lett., 25:2475-2478.

Cimino, G. et al. (1975), "Metabolism in Porifera-III. Chemical Patterns and the Classification of the Desmospongiae", Comp. Biochem. Physiol., 50B:279-285.

Cimino, G. et al., "Isolation and X-Ray Crystal Structure of a Novel Bromo-Compound from Two Marine Sponges" (1982), Tetrahedron Lett., 23:767-768.

Stempien, M. F. et al. (1972), "Isolation and Synthesis of Physiologically Active Substances from Sponges of the Genus *Agelas*", Abstracts of Papers, 164th National Meeting of the American Chemical Society, ACS, Washington, DC, Medi 21.

Minale, L. et al. (1976), "Natural Products from Porifera", Fortschr. Chem. Org. Naturst., 33:1-72.

Forenza, S. et al. (1971), "New Bromo-pyrrole Derivatives from the Sponge *Agelas oroides*", J. Chem. Soc., Chem. Commun., 1129-1130.

Garcia, E. E. et al. (1973), "Reinvestigation into the Structure of Oroidin, a Bromopyrrole Derivative from Marine Sponge" (1973), J. Chem. Soc. Chem. Comm., 78-79.

*Primary Examiner*—Henry R. Jiles
*Assistant Examiner*—Robert C. Whittenbaugh
*Attorney, Agent, or Firm*—Roman Saliwanchik; David R. Saliwanchik

[57] ABSTRACT

Novel bioactive metabolites from the Caribbean sponge *Agelas coniferin* are disclosed. These compounds are generically referred to as halopyrroles. They exhibit antiviral and antibacterial properties, and, thus, are useful for various non-therapeutic and therapeutic purposes.

31 Claims, No Drawings

BIOACTIVE METABOLITES FROM THE CARIBBEAN SPONGE *AGELAS CONIFERIN*

BACKGROUND OF THE INVENTION

The Caribbean Agelas sponges have been the source of a variety of bioactive products. Forenza et al. isolated 4,5-dibromopyrrole-2-carboxylic acid, its corresponding nitrile (Minale, L., Cimino, C., DeStefano, S. and Sodano, G. [1976] Fortschr. Chem. Org. Naturst. 33:1–72) and amide, and the antibiotic oroidin from *Agelas oroides* (Forenza, S., Minale, L., Riccio, R. and Fattorusso, E. [1971] J. Chem. Soc., Chem. Commun. 1129–1130; Garcia, E. E., Benjamin, L. E. and Fryer, R. I. [1973] J. Chem. Soc., Chem. Commun. 78–79). Oroidin has also been isolated from *Axinella damicornis, Axinella verrucosa,* and *Acanthella auranfiaca* (Cimino, G., DeStefano, S., Minale, L. and Sodano, G. [1975] Comp. Biochem. Physiol. 50B:279–285: Cimino, G., DeRosa, S. DeStefano, S., Mazzarella, L., Puliti, R. and Sodano, G. (1982) Tetrahedron Lett. 23:767,768). The KB carcinoma-altering antibiotic N-amidino-4-bromopyrrole-2-carboxamide was found in an Agelas sponge (Stempien, M. F., Jr., Nigrelli, R. F. and Chib, J. S. [1972] Abstracts of Papers, 164th National Meeting of the American Chemical Society, ACS, Washington, D. C. MEDI 21) while midpacamide and 4,5-dibromo-1-methyl-2-pyrrolecarboxylic acid were obtained from *Agelas cf. mauritiana* (Chevolot, L., Padwa, S., Ravi, B. N., Blyth, P. C. and Scheuer, P. J. [1977] Heterocycles 7:891–894; Chevolot, L. in Marine Natural Products, Chemical and Biological Perspectives, Scheurer, P. J., ed., Academic Press, NY, 1981, vol. 4, pp.54–92). Keramidine, a serotonergic receptor antagonist, was isolated from an Okinawan *Agelas* sp. sponge (Nakamura, H., Ohizumi, Y., Kobayashi, J. and Hirata, Y. [1984]Tetrahedron Lett. 25:2475–2478) while sceptrin (2b), isolated as the dihydrochloride, was reported to be the major antimicrobial constituent of *Agelas sceptrum* (Walker, R. P., Faulkner, D. J., Engen, D. V. and Clardy, J. [19811] J. Am. Chem. Soc. 103:6772–6773; Faulkner, D. J., U.S. Pat. No. 4,370,484, 1983; Chem Abstr. [1983] 98:155209x). Other compounds isolated include carotenoids (Buchecker, R., Eugster, C. H. and Litchfield, C [1977] Helv. Chim. Acta 60(8) #273: 2780–2788), sterols (Kanazawa, A., Teshima, S. and Hyodo, S. [1979]Comp. Biochem. Physiol. 62B:521–525; DiGiacomo, G., Dini, A., Falco, B., Marino, A. and Sica, D. [1983]Comp. Biochem. Physiol. 74B:499–501; Bohlin, L., Gehrken, H. P., Scheuer, P. J. and Djerassi, C. [1980] Steroids 35(3):295–304), antimicrobial (Cullen, E. and Devlin, J. P. [1975] Can. J. Chem. 53:1690–1691; Nakatsu, T., Faulkner, D. J., Matsumoto, G. K. and Clardy, J. [1984] Tetrahedron Lett. 25(9):935–938; Capon, R. J. and Faulkner, D. J. [1984] J. Am. Chem. Soc. 106:1819–1822) and Na- as well as K-ATPase inhibiting (Nakamura, H., Wu, H., Ohizumi, Y. and Hirata, Y. [1984] Tetrahedron Lett. 25(28):2989–2992; Wu, H., Nakamura, H., Kobayashi, J. and Ohizumi, Y. [1984] Tetrahedron Lett. 25(34):3719–3722 purinoditerpenes, and an antispasmodic, guanidinium-bearing sesquiterpene (Nakamura, H., Wu, H., Kobayashi, J., Ohizumi, Y., Hirata, Y, Higashijima, T. and Miyazawa, T. [1983] Tetrahedron Lett. 24(38):4105–4108).

BRIEF SUMMARY OF THE INVENTION

Seven novel bromopyrroles (1a, 3a-8a), as well as the known debromooroidin dimer sceptrin (2a) have been discovered in extracts of the Caribbean sponge *Agelas coniferin*. These compounds (Chart A), isolated as the diacetate salts, were found to be antibacterial and antiviral, and were active in barnacle settlement and biochemical prophage induction (BIA) assays. The structures given herein are based on spectroscopic comparisons to sceptrin and two-dimensional NMR data.

The invention also includes compounds as shown in Chart A wherein $X^1$, $X^2$, $X^3$, and $X^4$ can be Br, Cl, I, or H for both formulae I and II. These compounds can be readily made from the compounds disclosed herein by using standard procedures known in the art.

The compounds of the invention, generically referred to as halopyrroles herein, are useful for various non-therapeutic and therapeutic purposes. For example, because of the antiviral properties of the compounds, they are useful to swab laboratory benches and equipment in a virology laboratory to eliminate the presence of herpes simplex virus, type, I (HSV-1), or vesicular stomatitis virus (VSV). As disclosed infra, they are also useful prophylactically and therapeutically for treating viral infections.

Since the compounds of the invention have activity against gram positive and gram negative microorganisms as shown in Table 4, they can be used to treat humans and animals hosting such susceptible microbes by various means as hereinafter specifically delineated in the examples.

Further, the compounds of the invention can be used for treating breeding places of silkworms, to prevent or minimize infections which are well known to be caused by *Bacillus subtilis*. In general, the compounds of the invention, as the free base or their acid addition salts, can be used alone or in combination with other compounds to prevent the growth of or reduce the number of *Escherichia coli* or *B. subtilis* in various environments.

The activity of the compounds of the invention on the BIA assay indicates that the compounds have utility as anti-tumor agents. Thus, they can be used to treat humans and animals hosting susceptible tumors.

The activity of the compounds of the invention in the barnacle settlement assay permits the use of these compounds as antifouling agents for boats and ships. A solution of these compounds can be prepared by standard procedures and painted on the boats and ships, again using standard procedures, to reduce or prevent barnacle formation. The application of these compounds can be adjusted to meet the particular conditions of use and employ standard paint additives well known in the art.

Still further, the compounds of the invention can be used as ultraviolet screeners in the plastics industry since they effectively absorb UV rays.

DETAILED DISCLOSURE OF THE INVENTION

The novel bioactive compounds of the subject invention, designated 1a, and 3a–8a, can be obtained from extracts of the Caribbean Agelas sponge identified as Agelas coniferin. The known compound sceptrin (2a) also can be isolated from this sponge. This sponge is found in abundance at St. George's reef (−55 m) off the coast of Belize in the Caribbean, and, thus, can be readily obtained by standard scuba diving techniques.

When the sponge is collected it is stored at −20° C. until used to extract the novel compounds therefrom.

The initial step in the isolation of the novel compounds of the invention from *Agelas coniferin* is a pre-CCD (countercurrent distribution) solvent extraction procedure as shown in Chart B. The *A. coniferin* sample is denoted 30-VI-81-1-2. The ethyl acetate and 1-butanol layers were combined and dried to give a brown oil in 3.5% yield (from the wet sponge), whose mass spectrum (FABMS--fast atom bombardment mass spectrometry) indicated ions of m/z 541 (1Br)-619(2Br)-635(2Br)-697(3Br)-775(4Br) in a ratio of 13:100:13:4:2. This brown oil was partitioned by CCD (398-cycle; water:1-butanol:acetic acid : 10:8:1). The contents of selected tubes were analyzed by weight, FABMS, and reversed-phase high performance liquid chromatography (HPLC) (methanol:water:acetic acid:triethylamine : 800: 200:56:55; pH 4.8, 265 nm detection). On the basis of these results, the tubes were combined into 18 pooled fractions (called the "A4B" series; Table I).

These CCD fractions (Table I) contained seven major brominated compounds by FABMS. To obtain more of the 635(2Br) compound, and possibly others, the sponge AHCE 631 (*Agelas* cf. *mauritiana*) was extracted and partitioned as described above to give a dried, combined, ethyl acetate/1-butanol extract in a 2.5% yield (from the wet sponge). This was partitioned by CCD (400-tube; water:1-butanol:acetic acid : 10:8:1 containing 1% ethanol). The residues of various CCD fractions, were analyzed by weight and FABMS, and the fractions pooled on the basis of those results (forming the "C" series fractions; Table II).

Analytical-scale chromatographic evaluations were made of the fractions obtained by the CCD of the ethyl acetate and 1-butanol soluble materials. Since the bioactivity of the Agelas extracts had already been correlated with a series of brominated compounds, the HPLC separations were scaled up to isolate the UV-absorbing peaks which contained these brominated compounds. The eluants were flash evaporated, dried by high vacuum, and studied by NMR and FABMS. It was surprising to isolate two HPLC peaks containing m/z 619(2Br) and two peaks containing m/z 775(2Br). These four peaks were subsequently chromatographed by HPLC and studied by $^1$H NMR to verify the isolation of four unique, non-interconvertible compounds. It became clear that the brominated compounds with m/z values between 540 and 800 were being cleanly separated by HPLC, but $^1$H NMR spectra of the products indicated that residual triethylammonium acetate was not being totally removed by the high-vacuum treatment. Attempts to separate residual triethylammonium acetate from the sample included the use of chromatography on carbon, Sephadex G-10, Sephadex LH-20, Biogel P-2, and ion exchange resins, as well as countercurrent chromatography (CCC) and lyophilization. Based on the results of these studies, it was decided that the HPLC effluents would be treated by (in order): flash evaporation, multi-day desiccation at 0.1 torr in the presence of potassium hydroxide and concentrated sulfuric acid, solution in water followed by 0.4 μm filtration, then lyophilization and extended high vacuum drying to produce samples containing 5–10% triethylammonium acetate. The resulting powder was chromatographed on Sephadex LH-20 using chloroform-methanol-acetic acid (65:35:1), which eluted triethylammonium acetate prior to the compounds of interest. Acetic acid was required in the Sephadex mobile phase to obtain quantitative recovery and to prevent cross-contamination between sample batches. Lyophilization of the appropriate LH-20 eluants produced essentially pure compounds containing <1% triethylammonium acetate by $^1$H and $^{13}$C NMR.

Having developed a usable separation scheme, a larger quantity of an Agelas extract was used to produce enough material for structural studies. *Agelas coniferin* was targeted for study since it contained more of compounds 1a–8a than *Agelas* cf. *mauritiana*. The scaled-up isolation procedure started off with a pre-CCD solvent extraction as shown in Chart C. The acetone-insoluble portion of a methanolic extract of *Agelas coniferin* (2-VII-81-1-1) was dried to give 35.7 g of brown solids (3.4% yield from the wet sponge). FABMS and antibacterial and antiviral assays ensured that these solids contained the brominated, bioactive metabolites of interest. (Solids from the unfractionated, original methanol extract [called D1A] gave bioassay results of 0, 0, 0, 2 and 8, 7, 0, 4 mm, at 100 μg and 200 μg, respectively, in *E. coli* HSV-1, CV-1 monkey kidney cells and BIA assays. The acetone-insoluble fraction, called D1E, gave bioassay results of 9, 10, 0, 6 and 12, 11, 0, 9 mm, at 100 μg and 200 μg, respectively, in the same set of bioassays.) These solids from the fractionated extract were then partitioned by CCD (1036 steps—400 tubes; water:1-butanol:acetic acid: 10:8:1:1) to partially separate the brominated compounds of interest. The CCD fractions were pooled on the basis of FABMS, HPLC, and dried residue weight (Table III). This produced the largest of three sets of CCD pooled fractions, which were then used as sources of partially purified Agelas metabolites giving ions at (m/z) 541(1Br), 557(1Br), 619(2Br), 635(2Br), 697(3Br), and 775 (4Br).

Having previously worked out optimal purification procedures for compounds 1a–8a using the "A4B" and "C" series CCD fractions (vide supra), selected "D" series CCD fractions were subjected to reversed-phase HPLC using methanol-water-acetic acid-triethylamine mixtures (650–400:350–600:7–14:7–14). Chromatographic peaks which contained the brominated compounds of interest (by FABMS) were collected and dried, and the residues subjected to lyophilization and repeated LH-20 chromatography (chloroform:methanol:acetic acid:65:35:1) to produce the diacetate salts 1a–8a as amorphous solids. Compounds 1a–3a, 7a, and 8a were stable white solids, but 4a–6a were prone to discoloration and decomposition.

PHARMACOLOGICAL ACTIVITIES

Compounds 1a–8a have been screened for activity in antimicrobial, antiviral, cytotoxicity, and biochemical prophage induction (BIA) assays using 6.5-mm filter disk-agar diffusion methods: compounds 2a, 4a, and 8a were also submitted to barnacle settlement assays. Antibacterial assay results are reported in Table IV. Compounds 1a, 2a, and 4a–6a were the most active, inhibiting growth of *Bacillus subtilis* at 10 μg/disk. Compounds 2a, 4a, and 5a were also active against *Escherichia coli* at 10 μg/disk; by contrast, 7a was inactive at 100 μg/disk. All compounds were inactive against *Penicillium atrovenetum* and *Saccharomyces*, *cerevisiae* and were non-cytotoxic to monkey kidney (CV-1) cells at 200 μg/disk. Compounds 1a–6a were active against herpes simples virus, type I (HSV-1) at 20 μg/disk and against vesicular stomatitis virus (VSV) at 100 μg/disk; the more water soluble 7a and 8a produced only diffuse zones, with 7a being essentially inactive against HSV-1 and VSV at 200 μg/disk (Table V). In addition to these assay results, antiviral and cytotoxicity activities were verified by Dr. R. G. Hughes, Jr. (Roswell Park Memorial Institute), and are reported in Table VI.

In the BIA assay (Elespuru, R. K. and White, R. J. [1983] J. Cancer Res. 43:2819–2830) (Table VII), 1a, 2a and 8a were inducers at 10 μg/disk, 3a and 7a were somewhat less active, and compounds 414 6a were less active at 50 μg/disk. It is interesting that these compounds are BIA active, yet not cytotoxic. BIA activity, which indicates DNA interactions that inhibit protein replication, usually bears a strong correlation with cytotoxicity. It should be noted that 4a–6a gave reproducible, brown BIA assay responses instead of the normal red color. The reason for this is unknown. Several crude Agelas extracts studied in an Agelas survey also gave this brown response; these extracts were usually strongly cytotoxic.

Barnacle settlement assays (Standing, J. D., Hooper, I. R. and Costlow, J. D. [1984]J. Chem. Ecol. 10:823–834; Rittschof, D., Branscomb, E. S. and Costlow, J. D. [1984] J. Exp. Mar. Biol. Ecol. 82:131–146) on 2a, 4a, and 8a, using Balanus amphitrite amphitrite (Darwin, 1854), gave settlement-inhibition EC$_{50}$ values of 44 and 21 μg/mL for compounds 2a and 4a, respectively, and settlement-facilitation EC$_{50}$ values of 29 and 17 ng/mL for compounds 2a and 8a.

MATERIALS AND METHODS

Infrared and UV spectra were obtained on IBM IR/32 FTIR and Perkin-Elmer Lambda 3 UV/Vis spectrophotometers, respectively. Optical rotations were measured with a Rudolph Research Autopol III automatic polarimeter. NMR spectra were recorded on Varian XL-200, Nicolet NT-360 and NT-470, and General Electric QE-300 FT spectrometers using either methanol-d$_4$ as solvent and internal standard (δ 3.30 and 49.0) or in deuterium oxide using dioxane as an internal standard (δ 3.70 and 67.8). Mass spectra were run on MAT 311A, MAT 731, VG 7070-EH, ZAB-HF, or ZAB-SE spectrometers operating in the fast atom bombardment (FAB) mode using xenon atoms at 8–9 keV, typically using a matrix of either dithiothreitol:dithioerythritol (DT's, "magic bullet") (Witten, J. L., Schaffer, M. H., O'Shea, M., Cook, J. C., Hemling, M. E. and Rinehart, K. L., Jr. [1984] Biochem. Biophys. Res. Commun. 124:350–358) or thioglycerol. Tandem MS/MS FAB spectra were obtained on a VG ZAB (B-E-E-B) mass spectrometer (located at the National Institute for Environmental Health Sciences, Raleigh-Durham, N.C.) using collisionally-induced-decomposition (helium).

Countercurrent distributions (CCD's) were carried out on a 400-tube (20 mL/tube) 3-B-X Craig-Post automatic liquid-liquid fractionator, equipped with a fraction collector and typically set for 20 inversions per cycle with delays of 5–20 min. Countercurrent chromatography (CCC) was carried out in 1-butanol-water (1:1) with an Ito Multi-Layer Coil with Separator-Extractor from P.C. Inc., fit with a #10 column, a Milton Roy pump operating at 5.0 mL/min, and a Beckman model 153 fixed wavelength UV detector operating at 254 nm. Thin layer chromatography (TLC) used either EM Labs silica gel 60 F-254 glass plates (0.25 mm), Brinkman Polygram Sil G/UV plastic plates (0.25 mm), or Whatman KC-18 F reversed-phase glass plates. Normal phase plates were best developed using 1-butanol-water-acetic acid (4:1:1) and visualized with either UV (short and long wavelengths) or bromine. HPLC was performed on Beckman 114M, BEckman 110, and Waters M6000A pumps with Beckman 165, Beckman 153, and Waters 450 variable and fixed (254 nm) wavelength UV detectors. HPLC columns used were: Econosphere ODS (Alltech; 5 μm 4.6×250 mm or 10 μm−10×250 mm), Spherisorb ODS, ODS-2, and Phenyl (Alltech or Chromanetics; all 5 μm−4.6×250 mm), Altex ODS (5 μm−10×250 mm), Hamilton PRP-1 (10 μm−7×305 mm), Bondapak Cyanopropyl (Waters; 10 μm−3.9×300 mm), Econosphere Cyanopropyl (Alltech: 5 μm−4.6×250 mm), LiChrosorb Diol (Merck; 5 μm−4.6×250 mm), and Cyclobond I B-cyclodextrin (Astec; 5 μm−4.6×250 mm). Silica based ODS columns were operated with a guard column; either a Brownlee Spheri-5 (5 μm−4.6×30 mm), a Direct Connect Adsorbosphere ODS (Alltech; 5 μm−4.6 ×10 mm), or a hand-packed guard column packed with Bondapak C18/Corasil (Waters: 37–50 μm). Gravity flow chromatography (CHCl$_3$:MeOH:HOAc : 650:350:10) was carried out on Sephadex LH-20 (Pharmacia; 25–100 μm) in a 3×40-cm column equipped with a 254 nm detector, a chart recorder, and a fraction collector.

Samples IRCE 30-VI-81- 1-2 and IRCE 2-VII-81-1-1, identified as *Agelas coniferin*, were collected by SCUBA at St. George's reef (-55 m) off the coast of Belize in the Caribbean. Sample 20-III-78-1-4 ( =AHCE 631), identified as *Agelas cf. mauritiana* Carter 1883, was collected at Punta Oeste, Isla Roatan, Honduras (86° 38′ W 16° 15′ N) (-3 to -20 m). Preliminary bioactivities were determined in the field and at the University of Illinois. The sponges were stored at −20° C. until needed, then homogenized in appropriate solvents using a 33BL12 Waring Blender.

BIOLOGICAL ASSAYS

Antimicrobial activities were determined using the disc diffusion method on agar suspensions of *Escherichia coli, Bacillus subtilis, Saccharomyces cerevisia,* and *Penicillium atrovenetum*. Results are reported as the diameter (mm) of the clear zone of inhibited microbial growth surrounding a 6.5 mm filter paper disc treated with sample. Herpes simplex virus, type I (HSV-1; a DNA virus) and vesicular stomatitis (VSV; an RNA virus) grown on monkey kidney (CV-1) cells were used for the antiviral and cytotoxicity assays (Schroeder, A. C., Hughes, R. G., Jr. and Bloch, A. [1981] J. Med. Chem. 24:1078–1083). Cytotoxicity is always reported as the diameter (mm) of cell death (using neutral red dye) surrounding a 6.5 mm diameter filter paper disc. Antiviral activity is reported using one of two methods: a qualitative evaluation of viral plaque inhibition based on zone sizes using a +++ (strong), ++ (moderate), + (weak), ± (questionable), or − (negative) scale, or a quantitative evaluation which reports the zone diameter directly (in mm). The biochemical prophage induction assay (BIA) (Elespuru, R. K. and White, R. J. [1983] J. Cancer Res. 43:28192830), conducted with *E. coli* strain BR339, also used sample-impregnated 6.5 mm filter paper discs to obtain better quantitative data: results are reported as subjective evaluations of the test zone's size and color intensity on a scale of 0 (inactive: no color) to 10 (most active; strong red color). Barnacle settlement facilitation and inhibition assays were conducted by Dr. D. Rittschof at the Duke University Marine Labs, Beaufort, N.C.

Following are examples which illustrate procedures, including the best mode, for practicing the invention. These examples should not be construed as limiting. All percentages are by weight and all solvent mixture proportions are by volume unless otherwise noted.

Example 1—Preliminary Purifications—Small Sample

A 3.0-g sample of *Agelas coniferin* (IRCE 30-VI-81-1-2) was homogenized in 30 ml of methanol-toluene (3:1) and filtered to give a crude extract with cytotoxicity (antiviral) activities of 0(+) against CV-1 cells and HSV-1 (100 %1; 12.5 mm disk and 19 mm zones of inhibition against *B. subtilis* and *E. coli*. No activity against *S. cerevisiae* or *P. atrovenetum* was observed.

A 23-ml portion of the crude extract was treated with 46 ml of 1 M aqueous sodium nitrate, followed by washes with toluene (2×23 ml), dichloromethane (2×23 ml), ethyl acetate (3×30 ml), and 1-butanol (2×40 ml) (see Chart B). The antimicrobial activity was extracted into the ethyl acetate and 1-butanol fractions, giving zone sizes of 18.5 and 17 mm, respectively, against *B. subtilis* and zone sizes of 15.5 and 14.5 mm, respectively, against *E. coli*. The zone sizes of *B. subtilis* inhibition were equal both before and after the ethyl acetate and 1-butanol fractions were treated with: benchtop conditions (48 h), 80° C. heat (10 h), 0.5 M hydrochloric acid (480 h), or 0.5 M ammonium hydroxide (48 h). Bioautography of silica gel TLC plates correlated the antimicrobial activity with UV and iodine detectable compounds. FABMS analyses of preparative TLC fractions gave inconclusive results.

Example 2—Preliminary Purifications—Medium-Sized Sample

A 41-g sample of IRCE 30-VI-81-1-2 was extracted with methanol-toluene (3:1) and partitioned as above (see Chart B). FABMS of the ethyl acetate and 1-butanol fractions gave a major ion at m/z 619(2Br), a minor ion at m/z 541 (1Br), and ions in trace amounts at m/z 388(2Br), 417(1Br), 697(3Br), and 775(4Br). Normal-and reversed-phase TLC studies produced poor resolution and very low $R_f$ values for the antimicrobial and UV-absorbing compounds. A portion of the ethyl acetate layer was chromatographed into 45 fractions on Sephadex LH-20 (100% methanol; 18×350 mm column); the antibacterial components were not resolved. Dried solids (1.75 mg) from an antibacterial Sephadex LH-20 fraction were passed through a C-18 SEP-PAK with 4 ml of methanol to produce 1.48 mg (85%) of dried solids. This material (1.48 mg) was eluted through a silica gel SEP-PAK with 1.5 ml of methanol to produce 0.76 mg (51%) of a tan solid which produced a 21-mm zone of inhibition against *B. subtilis* (0.76 mg on a 12-mm disk). An identical 1.75 mg of dried, solid starting material, not subjected to either SEP-PAK, produced a 22-mm zone against *B. subtilis*.

A large aliquot of the ethyl acetate fraction was dried to produce 422 mg of solids. Based on the SEP-PAK studies, these solids were applied to a silica gel column (25×300 mm) and eluted with a methanol-acetone gradient, starting with methanol-acetone (20:80) and progressing steadily up to 100% methanol. Antibacterial activities (and visually colored materials) were located in bands throughout the resulting 100 7-ml fractions. FABMS indicated that fractions 13, 25, 41, and 92 all had major ions at m/z 619(2Br), 659(2Br), 699(2Br), and 581(1Br). The ions at m/z [541 +40(2Br)], [619+40(2Br)], and [619 +(2×40)(2Br)] indicated that acetone condensations had occurred with the free amine groups of sceptrin. This chromatographic process was not investigated further.

The original 1-butanol extract contained compounds giving [M+H]+ ions at m/z 619(2Br) and 541(2Br) in a ratio of 3:1 (FABMS). Reversed-phase HPLC of the 1-butanol extract, using methanol-water (85:15), produced peaks in which FABMS detected no brominated compounds. HPLC of the 1-butanol extract using methanol-water-1N sodium formate buffer (0.5N sodium formate—0.5N formic acid; pH 3.7) in a ratio of 700:250:50 also produced several major peaks. Collection and subsequent FABMS analysis of these chromatographic peaks located the peak containing only m/z 619(2Br), but a chromatographic peak containing m/z 541(1Br) was never found.

Dried solids (1.14 g) from the 1-butanol fraction were subjected to a 385 cycle countercurrent distribution (CCD) using 1-butanol-water-acetic acid (8:10:1). The resulting CCD fractions were dried with nitrogen and analyzed by FABMS. Ions with m/z of 619(2Br) and 541(1Br) were cleanly separated, and several intermediate CCD fractions contained mixtures of ions with m/z of 619(2Br) and 635(2Br). Chromatographic standards were obtained from tubes 135–165 ("541"), tubes 230–250 ("619"+"635"), and tubes 250–270 ("619").

Example 3—Batch Purifications (CCD)

"A4" Series

A 462-g sample of IRCE 30-VI-81-1-2 was homogenized with 4.5 L of methanol-toluene (3:1), and the filtered solution partitioned as per Chart B, using 4.5 L of 1M sodium nitrate, 700 ml of additional toluene, 2.1 L of chloroform (3×700 ml), 2.1 L of ethyl acetate (3×700 ml), and, after saturation of the aqueous layer with sodium chloride, 4 L of 1-butanol (4×1 L). The ethyl acetate and 1-butanol layers were combined and flash evaporated. The resulting thick brown syrup was dissolved in 500 ml of absolute ethanol, filtered to remove salts, and flash evaporated. Treatment again with absolute ethanol, followed by filtration, rotary evaporation, and drying in vacuo (0.3 mm, 24 h) gave 15.7 g (3.5% from the wet sponge) of a brown oil, whose mass spectrum (FABMS) indicated ions with m/z 541(1Br)-619(2Br)-635(2Br)-697(3Br)-775(4Br) in a ratio of 13:100:13:4:2.

The brown oil was partitioned in a 398-tube CCD using water-1-butanol-acetic acid (10:8:1). Long (25 min) delays were used to minimize emulsion problems. The entire contents of selected individual tubes were dried in streams of nitrogen and analyzed by weight, FABMS, and reversed-phase HPLC (methanol:water:acetic acid:triethylamine:800:200:56:55; pH 4.8, 265 nm detection). On the basis of residue weight of the dried fractions, ion intensities in FABMS, and partly guided by UV absorptions of unidentified HPLC peaks, the tubes were combined into 18 pooled fractions (See Table I). Samples A4BP, A4BR, and A4BS were individually subjected to CCD a second time.

"C" Series CCD

A 500-g sample of AHCE 631 was homogenized in 4 L of methanol-toluene (3:1) and worked up as described above (see Chart B) to give a combined ethyl acetate/1-butanol extract with a dry weight of 12.5 g (2.5% from the wet sponge). This was partitioned in a 400-tube CCD using water-1-butanol-acetic acid (10:8:1) containing 1% ethanol. After evaporation in a stream of nitrogen, the residues of various fractions were analyzed by weight and FABMS, and the fractions combined as shown in Table II. These pooled fractions were subjected to HPLC to test for the presence of brominated metabolites other than 1a-8a.

"D" Series CCD

A 1040-g sample of IRCE 2-VII-81-1-1 (*Agelas coniferin*) was homogenized and washed with 8 L (4×2 L) of methanol (see Chart C). The filtered methanolic solution was flash evaporated and dried in vacuo to a brown oil. This oil was triturated with 800 ml of methanol to produce a suspension which was filtered, flash evaporated, and dried in vacuo to 41.5 g of brown solids. These solids were washed and filtered with acetone (2×250 ml) at 40° C., and the retained solids were triturated with methanol (2×250 ml). The filtered methanolic solution was flash evaporated and dried in vacuo to produce 35.7 g of sample D1E (3.4% yield from the wet sponge). FABMS and antibacterial and antiviral assays ensured that sample D1E contained the brominated bioactive metabolites of interest.

Sample D1E (35.6 g) was partitioned by CCD (1036 steps—400 tubes) using water-1-butanol acetic acid-ethanol (10:8:1:1). The mobile phase was eluted after tube 400 and diverted to a fraction collector which combined every two successively-eluted mobile phase aliquots. The effluents were analyzed by dried residue weight and FABMS and combined as shown in Table III.

Example 4—Final Purifications, Including HPLC

Compounds 1a-6a were isolated from the pooled CCD fractions (Table III) in a similar manner. Pooled fractions containing the compounds of interest were individually subjected to reversed-phase (C18) preparative HPLC using various combinations of water-methanol-acetic acid-triethylamine (650-400:350-600-:7-14:7-14 v/v; pH 5) on Econosphere ODS 5 μm—4.6×250 mm and 10 μm—10×250 mm columns. More heavily brominated compounds required the higher percentages of methanol for elution. Samples were chromatographed 1–3 times, using larger k′ values generated by lower methanol/water ratios, until pure by analytical HPLC. HPLC fractions containing the brominated compounds of interest were flash evaporated and dried at 0.2 torr for several days over sulfuric acid and potassium hydroxide. The resulting oil was dissolved in water, filtered (0.4 μm), and lyophilized, and the solids subjected to repeated, LH-20 chromatography (1–3 times over a 3×40 cm column using CHCl$_3$:MeOH:HOAc:65:35:1) to remove all of the faster-eluting triethylammonium acetate. The appropriate LH-20 fractions, as analyzed by $^1$H NMR, were lyophilized to produce the diacetate salts, compounds 1a-6a, as amorphous, white-to-tan solids. The isolations of 7a and 8a required a modification of this technique. Colored impurities could be removed either by eluting the acetate salts as hydrochlorides from Dowex 1×2 (C1−) with dilute hydrochloric acid, or much less efficiently, by passing the acetate salts over a column of Sephadex G-10 with 5% acetic acid in water.

The CCD fractions from Table I (the "A4" series) were used to develop these optimal isolation techniques; the CCD fractions from Table III ("D" series) were used for quantitative isolations as disclosed herein. HPLC of the "C" series of CCD fractions also produced 1a-8a, but in different amounts, and resulted in the isolation of uncharacterized compounds.

Example 5—Debromosceptrin Acetate (1a)

Sample D1EG (Table III) was subjected to HPLC using water-methanol-acetic acid-triethylamine (600:400:7:7) to give a single, main, UV-absorbing peak, which was worked up as described above, including 3 passages over LH-20, to give 92.2 mg of essentially pure 1a: $[\alpha]_D^{25}$ −0.3° (c 1.03, MeOH); UV (MeOH) $\lambda_{max}$ 203 nm (ε 25 700), 212 (26 700), 265 (25 600); IR (KBr) 3350 (Br), 1682, 1618, 1565, 1528, 1409, 1330, 922 cm$^{-1}$.

Anal. Calcd for $C_{22}H_{26}$ $^{79}BrN_{10}O_2$ (M+H): 541.1424. Found: 541.1434 (HRFABMS).

Example 6—Sceptrin Acetate (2a) and Ageliferin Acetate (4a)

Sample D1EN (Table III) was subjected to preparative HPLC in forty equal portions using water-methanol-acetic acid-triethylamine (500:500:7:7) to give two main UV-absorbing peaks which flanked a series of smaller peaks. The larger, early-eluting major peak was rechromatographed in the same HPLC system, and worked up as described above, subjecting it twice, in three portions, to LH-20 chromatography to give 311.8 mg of essentially pure 2a: $[\alpha]_D^{25}-0.3°$ (c 1.10, MeOH); UV (MeOH) $\lambda_{max}$ 205 nm ($\epsilon$ y27 300), 214 (28 300), 267 (25 200); IR (KBr) 3350 (br), 1683, 1624, 1566, 1527, 1408, 1332, 922 $cm^{-1}$. Anal Calcd for $C_{22}H_{25}^{79}Br^{81}BrN_{10}O_2$ (M+H): 621.0508. Found: 621.0520 (HRFABMS).

The smaller, later eluting peak was also rechromatographed by HPLC, and was then worked up in a similar manner (two passages over LH-20) to give 43.3 mg of essentially pure 4a: $[\alpha]_D^{25}-1.3°$ (c 0.135, MeOH); UV (MeOH $\lambda_{max}$ 204 nm ($\epsilon$ 25 500), 220 (27 100), 267 (25 900); IR (KBr) 3350 (br), 1681, 1629, 1565, 1526, 1407, 1330, 922 $cm^{-1}$. Anal. Calcd for $C_{22}H_{25}^{79}Br^{81}BrN_{10}O_2$ (M+H): 621.0508. Found: 621.0526 (HRFABMS).

Example 7—Dibromosceptrin Acetate (3a), Bromoageliferin Acetate (5a), and Dibromoageliferin Acetate (6a)

Samples D1ER through D1EU (Table III; total weight 840.6 mg) were separately subjected (in small portions) to HPLC using water-methanol-acetic acid-triethylamine (350-370:650-630:7:7) to give a large number of UV-absorbing peaks which were collected and analyzed by FABMS and NMR. Three of the major peaks were shown to contain compounds 3a, 5a, and 6a. The earliest of these three peaks was rechromatographed twice by HPLC, subjected to LH-20 chromatography, then rechromatographed by HPLC (water:methanol:acetic acid:triethylamine:400:600:14:14). It was then worked up as described above to give 18.5 mg of essentially pure 5a: $[\alpha]_D^{25}-0.2°$ (c 0.175, MeOH); UV (Meoh) $\lambda_{max}$ 203 nm ($\epsilon$ 30 600), 220 (26 300), 270 (24 500); IR (KBr) 3400 (br), 1684, 1652, 1627, 1565, 1525, 1410, 1327, 922 $cm^{-1}$. Anal. Calcd for $C_{22}H_{24}^{79}Br_2^{81}BrN_{10}O_2$ (M+H): 698.9613. Found: 698.9608 (HRFABMS).

The intermediate of these three peaks was rechromatographed by HPLC and worked up as described above (once through LH-20) to give 6.6 mg of essentially pure 3a: $[\alpha]_D^{25}-0.4°$ (c 0.108, MeOH); UV (MeOH) $\lambda_{max}$ 202 nm ($\epsilon$ 27 300), 215 (24 800), 273 (26 300); IR (KBr) 3350 (br), 1635, 1568, 1527, 1414, 1327, 924 $cm^{-1}$. Amal. Calcd for $C_{22}H_{23}^{79}Br_2^{81}Br_2N_{10}O_2$ (M+H): 778.8698. Found: 778.8712 (HRFABMS).

The latest eluting of these three peaks was rechromatographed by HPLC and worked up as described above (chromatographed twice on LH-20) to give 42.8 mg of essentially pure 6a: $[\alpha]_D^{25}-0.3°$ (c 0.164, MeOH); UV (MeOH) $\lambda_{max}$ 202 nm ($\epsilon$ 24 300), 214 (24 500), 274 (25 000); IR (KBr) 3400 (br), 1684, 1631, 1570, 1526, 1415, 1328 $cm^{-1}$. Anal. Calcd for $C_{22}H_{23}^{79}Br_2N_{10}O_2$ (M+H): 778.8698. Found: 778.8698 (HRFABMS).

Example 8—Debromooxysceptrin Acetate (7a)

Samples D1EE and D1EF (Table III; total weight 435.8 mg) were separately repeatedly subjected to chromatography on LH-20 (chloroform:methanol:acetic acid:65:35:1) to remove the faster eluting debromosceptrin (1a) from 7a. Fractions containing 7a but devoid of 1a (as determined by HPLC and $^1H$ NMR) were pooled and subjected to reversed-phase HPLC using water-methanol-acetic acid-triethylamine (600:400:14:14). The major UV-absorbing peak was worked up as described above to give 7.0 mg of essentially pure 7a: $[\alpha]_D^{25}-0.2°$ (c 0.108, MeOH); UV (MeOH) $\lambda_{max}$ 203 nm ($\epsilon$ 32 400), 220 (24 600), 265 (26 600); IR (KBr) 3350 (br), 1685, 1632, 1568, 1531, 922 $cm^{-1}$. Anal. Calcd for $C_{22}H_{26}^{79}BrN_{10}O_3$ (M+H): 557.1373. Found: 557:1363 (HRFABMS).

Example 9—Oxysceptrin Acetate (8a)

Samples D1EI and D1EJ (Table III; total weight 1518 mg) were separately subjected to chromatography on LH-20 (chloroform:methanol:acetic acid:65:35:1) to remove any of the faster eluting sceptrin (2a). Fractions containing oxysceptrin but no sceptrin (as determined by HPLC and $^1H$ NMR; total weight 701 mg) were pooled and subjected to reversed-phase HPLC using water-methanol-acetic acid-triethylamine (500:500:14:14). The major UV-absorbing peak was worked up as described above (being subjected to LH-20 chromatography in three batches) to give 342 mg of essentially pure 8a: $[\alpha]_D^{25}-0.04°$ (c 1.37, MeOH); UV (MeOH) $\lambda_{max}$ 203 nm ($\epsilon$ 35 100), 221 (30 700), 267 (28 100); IR (KBr) 3350 (br), 1681, 1632, 1565, 1523, 921 $cm^{-1}$. Anal. Calcd for $C_{22}H_{25}^{79}Br^{81}BrN_{10}O_3$ (M+H): 637.0457. Found: 637.0472 (HRFABMS).

Example 10—Formation of the Dihydrochloride Salts 2b, 4b, and 8b

Compounds 2b, 4b, and 8b were formed quantitatively from their respective diacetate salts (2a, 4a, and 8a) by treatment with 0.1N HCl (30 mol equiv), followed by flash evaporation and desiccation in vacuo. Compound 2b: IR (KBr) 3300 (br), 1677, 1564, 1523, 921 $cm^{-1}$; (Lit$^2$ $[\alpha]_D^{25}-7.4°$ (c 1.2, MeOH); UV (MeOH) $\lambda_{max}$ 265 nm ($\epsilon$ 20 850). Compound 4b: IR (KBr) 3350 (br), 1677, 1622, 1565, 1522, 922 $cm^{-1}$. Compound 8b: IR (KBr) 3300 (br), 1776, 1678, 1627, 1565, 1524, 921 $cm^{-1}$. Colored impurities in 2b were removed either with activated charcoal (DARCO) or by passing 2b over Dowex 1×2 [Cl$^-$] ion exchange resin with water. Decolored material tended to crystallize.

Example 11—Formation of the Free Base Form of 2a

The free base form of 2a was made by treating a solution of 10 mg of the acetate salt in 2 ml of water with a saturated solution of 24 mg (18 eq of sodium carbonate in water. When the solution was extracted twice with 2 ml of ethyl acetate, virtually all color was extracted into the ethyl acetate layer, which was dried with magnesium sulfate, evaporated to dryness, and desiccated in vacuo to a yellow glass.

The free base form of the other compounds of the invention can be made by using essentially the same process as described above.

Since the compounds of the invention are basic, they form salts with mineral acids such as HCl, H$_2$SO$_4$, H$_3$PO$_4$, and the like. Such salts can be prepared by suspending the compounds in water, adding a dilute acid until the pH of the solution is about 3 to 4, and freeze-drying the solution to provide a dried residue of the salt. Salts can be used for the same biological purposes as the parent compounds.

The compounds of the invention have free amino groups available for derivatization. Thus, acyl amides can be prepared by use of standard acylating conditions well known to those skilled in the art. Acyl derivatives can be used for the same biological purposes as the parent compounds.

Acids which can be used in the acylation include (a) saturated or unsaturated, straight or branched chain aliphatic carboxylic acids, for example, acetic, propionic, butyric, isobutyric, tert-butylacetic, valeric, isovaleric, caproic, caprylic, decanoic, dodecanoic, lauric, tridecanoic, myristic, pentadecanoic, palmitic, margaric, stearic, acrylic, crotonic, undecylenic, oleic, hexynoic, heptynoic, octynoic acids, and the like; (b) saturated or unsaturated, alicyclic carboxylic acids, for example, cyclobutanecarboxylic acid, cyclopentanecarboxylic acid, cyclopentenecarboxylic acid, methylcyclopentenecarboxylic acid, cyclohexanecarboxylic acid, dimethylcyclohexanecarboxylic acid, dipropylcyclohexanecarboxylic acid, and the like; (c) saturated or unsaturated, alicyclic aliphatic carboxylic acids, for example, cyclopentaneacetic acid, cyclopentanepropionic acid, cyclohexaneacetic acid, cyclohexanebutyric acid, methylcyclohexaneacetic acid, and the like; (d) aromatic carboxylic acids, for example, benzoic acid, toluic acid, naphthoic acid, ethylbenzoic acid, isobutylbenzoic acid, methylbutylbenzoic acid, and the like; and (e) aromatic-aliphatic carboxylic acids, for example, phenylacetic acid, phenylpropionic acid, phenylvaleric acid, cinnamic acid, phenylpropiolic acid and naphthylacetic acid, and the like. Suitable halo-, nitro-, hydroxy-, keto-, amino-, cyano-, thiocyano-, and lower alkoxyhydrocarbon carboxylic acids include hydrocarboncarboxylic acids as given above which are substituted by one or more of halogen, nitro, hydroxy, keto, amino, cyano, or thiocyano, or lower alkoxy, advantageously lower alkoxy of not more than six carbon atoms, for example, methoxy, ethoxy, propoxy, butoxy, amyloxy, hexyloxy, and isomeric forms thereof. Examples of such substituted hydrocarbon carboxylic acids are: mono-, di-, and trichloroacetic acid; α- and β-chloropropionic acid: α- and γ-bromobutyric acid; α- and δ-iodovaleric acid; mevalonic acid; 2- and 4-chlorocyclohexanecarboxylic acid; shikimic acid; 2-nitro-1-methyl-cyclobutanecarboxylic acid; 1,2,3,4,5,6-hexachlorocyclohexanecarboxylic acid; 3-bromo-2-methylcyclohexanecarboxylic acid; 4- and 5-bromo-2-methylcyclohexanecarboxylic acid; 5- and 6-bromo-2-methylcyclohexanecarboxylic acid; 2,3-dibromo-2-methylcyclohexanecarboxylic acid; 2,5-dibromo-2-methylcyclohexanecarboxylic acid; 4,5-dibromo-2-methylcyclohexanecarboxylic acid; 5,6-dibromo-2-methylcyclohexanecarboxylic acid; 3-bromo-3-methylcyclohexanecarboxylic acid; 6-bromo-3-methylcyclohexanecarboxylic acid; 1,6-dibromo-3-methylcyclohexanecarboxylic acid; 2-bromo-4-methylcyclohexanecarboxylic acid; 1,2-dibromo-4-methylcyclohexanecarboxylic acid; 3-bromo-2,2,3-trimethylcyclopentanecarboxylic acid; 1-bromo-3,5-dimethylcyclohexanecarboxylic acid; homogentisic acid, o-, m-, and p-chlorobenzoic acid; anisic acid; salicylic acid; p-hydroxybenzoic acid; β-resorcylic acid; gallic acid; veratric acid; trimethoxybenzoic acid; trimethoxycinnamic acid; 4,4'-dichlorobenzilic acid; o-, m-, and p-nitrobenzoic acid; cyanoacetic acid; 3,4- and 3,5-dinitrobenzoic acid; 2,4,6-trinitrobenzoic acid; thiocyanoacetic acid; cyanopropionic acid; lactic acid; ethoxyformic acid (ethyl hydrogen carbonate); malic acid; citric acid; isocitric acid; 6-methylsalicylic acid; mandelic acid; levulinic acid; pyruvic acid; glycine; alanine; valine; isoleucine; leucine; phenylalanine; proline, serine, threonine; tyrosine; hydroxyproline; ornithine; lysine; arginine; histidine; hydroxylysine, phenylglycine; p-aminobenzoic acid; m-aminobenzoic acid; anthranilic acid; aspartic acid; glutamic acid; aminoadipic acid; glutamine; asparagine; and the like.

Compounds other than those specifically exemplified herein, i.e., compounds 1a-8a, which come within the scope of this invention, as shown in Chart A, wherein $X^1$, $X^2$, $X^3$, and $X^4$ can be Br, Cl, or I for both formulae I and II, can be prepared by standard procedures known in the art of bromination, chlorination, iodination, or dehalogenation.

The administration of halopyrroles is useful prophylactically and therapeutically for treating microbial and viral infections. For example, pharmaceutical compositions containing the active ingredients are useful in prophylactic or therapeutic treatment of humans and animals infected or likely to be infected with herpes simplex virus, type I (HSV-1) or vesicular stomatitis virus (VSV), and gram positive or gram negative microbes, e.g., *B. subtilis* and *E. coli*.

The dosage administered will be dependent upon the identity of the viral infection, the type of host involved, its age, health, weight, kind of concurrent treatment, if any, frequencey of treatment and therapeutic ratio.

Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

Expressed in terms of concentration, an active ingredient can be present in the compositions of the present invention for localized use about the cutis, intranasally, pharyngolaryngeally, bronchially, broncholially, intravaginally, rectally, or ocularly in a concentration of from about 0.01 to about 50% w/w of the composition; preferably about 1 to about 20% w/w of the composition; and for parenteral use in a concentration of from about 0.05 to about 50% w/v of the composition and preferably from about 5 to about 20% w/v.

The compositions of the present invention are preferably presented for administration to humans and animals in unit dosage forms, such as tablets, capsules, pills, powders, granules, suppositories, sterile parenteral solutions or suspensions, sterile non-parenteral solutions or suspensions, and oral solutions or suspensions and the like, containing suitable quantities of an active ingredient.

For oral administration either solid or fluid unit dosage forms can be prepared.

Powders are prepared quite simply by comminuting the active ingredient to a suitable fine size and mixing with a similarly comminuted diluent. The diluent can be an edible carbohydrate material such as lactose or starch. Advantageously, a sweetening agent or sugar is present as well as a flavoring oil.

Capsules are produced by preparing a powder mixture as hereinbefore described and filling into formed gelatin sheaths. Advantageously, as an adjuvant to the filling operation, a lubricant such as talc, magnesium stearate, calcium stearate and the like is added to the powder mixture before the filling operation.

Soft gelatin capsules are prepared by machine encapsulation of a slurry of active ingredients with an acceptable vegetable oil, light liquid petrolatum or other inert oil or triglyceride.

Tablets are made by preparing a powder mixture, granulating or slugging, adding a lubricant and pressing into tablets. The powder mixture is prepared by mixing an active ingredient, suitably comminuted, with a diluent or base such as starch, lactose, kaolin, dicalcius phosphate and the like. The powder mixture can be granulated by wetting with a binder such as corn syrup, gelatin solution, methylcellulose solution or acacia mucilage and forcing through a screen. As an alternative to granulating, the powder mixture can be slugged, i.e., run through the tablet machine and the resulting imperfectly formed tablets broken into pieces (slugs). The slugs can be lubricated to prevent sticking to the tablet-forming dies by means of the addition of stearic acid, a stearic salt, talc or mineral oil. The lubricated mixture is then compressed into tablets.

Advantageously the tablet can be provided with a protective coating consisting of a sealing coat or enteric coat of shellac, a coating of sugar and methylcellulose and polish coating of carnauba wax.

Fluid unit dosage forms for oral administration such as syrups, elixirs and suspensions can be prepared wherein each teaspoonful of composition contains a predetermined amount of active ingredient for administration. The water-soluble forms can be dissolved in an aqueous vehicle together with sugar, flavoring agents and preservatives to form a syrup. An elixir is prepared by using a hydroalcoholic vehicle with suitable sweeteners together with a flavoring agent. Suspensions can be prepared of the insoluble forms with a suitable vehicle with the aid of a suspending agent such as acacia, tragacanth, methylcellulose and the like.

For parenteral administration, fluid unit dosage forms are prepared utilizing an active ingredient and a sterile vehicle, water being preferred. The active ingredient, depending on the form and concentration used, can be either suspended or dissolved in the vehicle. In preparing solutions the water-soluble active ingredient can be dissolved in water for injection and filter sterilized before filling into a suitable vial or ampule and sealing. Advantageously, adjuvants such as a local anesthetic, preservative and buffering agents can be dissolved in the vehicle. Parenteral suspensions are prepared in substantially the same manner except that an active ingredient is suspended in the vehicle instead of being dissolved and sterilization cannot be accomplished by filtration. The active ingredient can be sterilized by exposure to ethylene oxide before suspending in the sterile vehicle. Advantageously, a surfactant or wetting agent is included in the composition to facilitate uniform distribution of the active ingredient.

In addition to oral and parenteral administration, the rectal and vaginal routes can be utilized. An active ingredient can be administered by means of a suppository. A vehicle which has a melting point at about body temperature or one that is readily soluble can be utilized. For example, cocoa butter and various polyethylene glycols (Carbowaxcs) can serve as the vehicle.

For intranasal instillation, fluid unit dosage forms are prepared utilizing an active ingredient and a suitable pharmaceutical vehicle, water being preferred, or by dry powder for insufflation.

The active ingredients can also be admixed in animal feed. The active ingredients can conveniently be prepared in the form of a food premix. The food premix can comprise an active ingredient in admixture with an edible pharmaceutical diluent such as starch, oatmeal, flour, calcium carbonate, talc, dried fish meal and the like nontoxic, orally acceptable pharmaceutical diluents. The prepared premix is then conveniently added to the regular feed.

For use as aerosols the active ingredients can be packaged in a pressurized aerosol container together with a gaseous or liquefied propellant, for example, dichlorodifluoromethane, carbon dioxide, nitrogen, propane, and the like, with the usual adjuvants such as cosolvents and wetting agents, as may be necessary or desirable.

The term "unit dosage form" as used in the specification and claims refers to physically discrete units suitable as unitary dosages for human and animal subjects, each unit containing a predetermined quantity of active material calculated to produce the desired therapeutic effect in association with the required pharmaceutical diluent, carrier or vehicle. The specifications for the novel unit dosage forms of this invention are dictated by and are directly dependent on (a) the unique characteristics of the active material and the particular therapeutic effect to be achieved, and (b) the limitation inherent in the art of compounding such an active material for therapeutic use in humans, as disclosed in this specification, these being features of the present invention. Examples of suitable unit dosage forms in accord with this invention are tablets, capsules, troches, suppositories, powder packets, wafers, cachets, teaspoonfuls, tablespoonfuls, dropperfuls, ampuls, vials, segregated multiples of any of the foregoing, and other forms as herein described.

The active ingredients to be employed as antimicrobial or antiviral agents can be easily prepared in unit dosage form with the employment of pharmaceutical materials which themselves are available in the art and can be prepared by established procedures. The following preparations are illustrative of the preparation of the unit dosage forms of the present invention, but are not intended to be limiting.

EXAMPLE 12

Hard-Gelatin Capsules

One thousand two-piece hard gelatin capsules for oral use, each capsule containing 100 mg of a halopyrrole are prepared from the following types and amounts of ingredients:

| | |
|---|---|
| A halopyrrole, micronized | 100 gm |
| lactose | 100 gm |
| corn starch | 20 gm |
| talc | 20 gm |
| magnesium stearate | 2 gm |

The halopyrrole, finely divided by means of an air micronizer, is added to the other finely powdered ingredients, mixed thoroughly and then encapsulated in the usual manner.

The foregoing capsules are useful for preventing or treating microbial or viral infections by the oral administration of one or two capsules one to four times a day.

Using the procedure above, capsules are similarly prepared containing a halopyrrole in 50, 250 and 500 mg amounts by substituting 50 gm, 250 gm and 500 gm of halopyrrole for the 100 gm used above.

EXAMPLE 13

Soft Gelatin Capsules

One-piece soft gelatin capsules for oral use, each containing 250 mg of a halopyrrole (finely divided by means of an air micronizer), are prepared by first suspending the compound in 0.5 ml of corn oil to render the material capsulatable and then capsulating in the above manner.

The foregoing capsules are useful for preventing or treating microbial or viral infections by the oral administration of one or two capsules one to four times a day.

EXAMPLE 14

Tablets

One thousand tablets, each containing 500 mg of a halopyrrole are prepared from the following types and amounts of ingredients:

| | |
|---|---|
| a halopyrrole, micronized | 500 gm |
| lactose | 75 gm |
| corn starch | 50 gm |
| magnesium stearate | 4 gm |
| light liquid petrolatum | 5 gm |

The halopyrrole, finely divided by means of an air micronizer, is added to the other ingredients and then thoroughly mixed and slugged. The slugs are broken down by forcing through a Number Sixteen screen. The resulting granules are then compressed into tablets, each tablet containing 500 mg of the halopyrrole.

The foregoing tablets are useful for preventing or treating microbial or viral infections by the oral administration of one or two tablets one to four times a day.

Using the procedure above, tablets are similarly prepared containing a halopyrrole in 250 mg and 100 mg amounts by substituting 250 gm and 10 gm of a halopyrrole for the 500 gm used above.

EXAMPLE 15

Oral Suspension

One thousand ml of an aqueous suspension for oral use, containing in each teaspoonful (5 ml) dose, 500 mg of a halopyrrole, is prepared from the following types and amounts of ingredients:

| | |
|---|---|
| a halopyrrole, micronized | 100 gm |
| citric acid | 2 gm |
| benzoic acid | 1 gm |
| sucrose | 700 gm |
| tragacanth | 5 gm |
| lemon oil | 2 gm |
| deionized water, q.s. | 1000 ml |

The citric acid, benzoic acid, sucrose, tragacanth and lemon oil are dispersed in sufficient water to make 850 ml of suspension. The halopyrrole, finely divided by means of an air micronizer, is stirred into the syrup until uniformly distributed. Sufficient water is added to make 1000 ml.

The composition so prepared is useful for preventing or treating microbial or viral infections at a dose of 1 tablespoonful (15 ml) three times a day.

EXAMPLE 16

A sterile aqueous suspension for parenteral injection, containing in 1 ml 300 mg of a halopyrrole, is prepared from the following types and amounts of ingredients:

| | |
|---|---|
| a halopyrrole, micronized | 300 gm |
| polysorbate 80 | 5 gm |
| methylparaben | 2.5 gm |
| propylparaben | 0.17 gm |
| water for injection, q.s. | 1000 ml |

All the ingredients, except the halopyrrole, are dissolved in the water and the solution sterilized by filtration. To the sterile solution is added the sterilized halopyrrole, finely divided by means of an air micronizer, and the final suspension is filled into sterile vials and the vials sealed.

The composition so prepared is useful for preventing or treating microbial or viral infections at a dose of 1 ml (1M) three times a day.

EXAMPLE 17

Suppository, Rectal and Vaginal

One thousand suppositories, each weighing 2.5 gm and containing 150 mg of a halopyrrole are prepared from the following types and amounts of ingredients:

| | |
|---|---|
| a halopyrrole, micronized | 150 gm |
| propylene glycol | 150 gm |
| polyethylene glycol #4000, q.s. | 2,500 gm |

The halopyrrole is finely divided by means of an air micronizer and added to the propylene glycol and the mixture passed through a colloid mill until uniformly dispersed. The polyethylene glycol is melted and the propylene glycol dispersion added slowly with stirring. The suspension is poured into unchilled molds at 40° C. The composition is allowed to cool and solidify and then removed from the mold and each suppository foil wrapped.

The foregoing suppositories are inserted rectally or vaginally for preventing or treating microbial or viral infections.

EXAMPLE 18

Intranasal Suspension

One thousand ml of a sterile aqueous suspension for intranasal instillation, containing in each ml 150 mg of a halopyrrole, is prepared from the following types and amounts of ingredients:

| | |
|---|---|
| a halopyrrole, micronized | 150 gm |
| polysorbate 80 | 5 gm |
| methylparaben | 2.5 gm |
| propylparaben | 0.17 gm |
| deionized water, q.s. | 1000 ml |

All the ingredients, except the halopyrrole, are dissolved in the water and the solution sterilized by filtration. To the sterile solution is added the sterilized halopyrrole, finely divided by means of an air micronizer, and the final suspension is aseptically filled into sterile containers.

The composition so prepared is useful for preventing or treating microbial or viral infections by intranasal instillation of 0.2 to 0.5 ml given one to four times per day.

EXAMPLE 19

Animal Feed

One thousand grams of feed premix is prepared from the following types and amounts of ingredients:

| | |
|---|---|
| a halopyrrole | 20 gm |
| soybean meal | 400 gm |
| fish meal | 400 gm |
| wheat germ oil | 50 gm |
| sorghum molasses | 130 gm |

The ingredients are mixed together and pressed into pellets.

The premix can be fed directly to laboratory animals, i.e., rats and mice, for preventing or treating microbial or viral infections.

For larger animals the premix can be added to the animal's regular feed in an amount calculated to give the desired dose of halopyrrole. For example, one part of premix is added to 2.5 parts of a cat's regular feed to provide the desired dose of 200 mg/kg/day for a cat of 2.5 kg.

An active ingredient can also be present, as shown in Examples 20–22 in the undiluted pure form for use locally about the cutis, intranasally, pharyngolaryngeally, bronchially, broncholially or orally.

EXAMPLE 20

Powder

Five hundred grams of a halopyrrole in bulk form is finely divided by means of an air micronizer. The micronized powder is placed in a shaker-type container.

The foregoing composition is useful for preventing or treating microbial or viral infections at localized sites by applying the powder one to four times per day.

EXAMPLE 21

Oral Powder

One thousand grams of a halopyrrole in bulk form is finely divided by means of an air micronizer. The micronized powder is divided into individual doses of 250 mg and packaged.

The foregoing powders are useful for preventing or treating microbial or viral infections by the oral administration of one or two powders suspended in a glass of water, one to four times per day.

EXAMPLE 22

Insufflation

One thousand grams of a halopyrrole in bulk form is finely divided by means of an air micronizer.

The foregoing composition is useful for preventing or treating microbial or viral infections by the inhalation of 30 to 75 mg one to four times per day.

CHART A

Formula I.

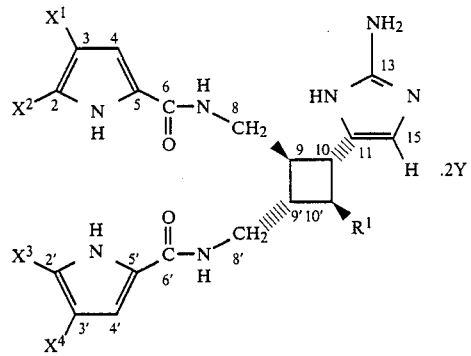

| | $X^1$ | $X^2$ | $X^3$ | $X^4$ | $R^1$ | Y |
|---|---|---|---|---|---|---|
| 1a | Br | H | H | H | A | HOAc |
| 2a | Br | H | H | Br | A | HOAc |
| 2b | Br | H | H | Br | A | HCl |
| 3a | Br | Br | Br | Br | A | HOAc |

CHART A-continued

| | $X^1$ | $X^2$ | $X^3$ | $X^4$ | A/B | Y |
|---|---|---|---|---|---|---|
| 7a | Br* | H | H | H* | B | HOAc |
| 8a | Br | H | H | Br | B | HOAc |
| 8b | Br | H | H | Br | B | HCl |

Formula II.

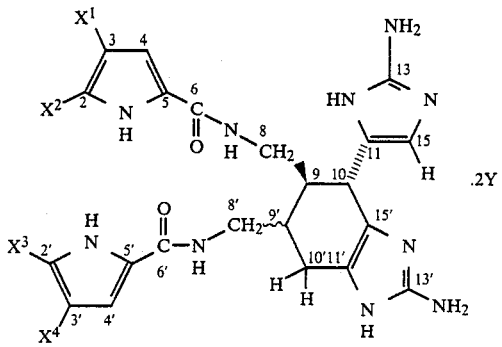

| | $X^1$ | $X^2$ | $X^3$ | $X^4$ | Y |
|---|---|---|---|---|---|
| 4a | Br | H | H | Br | HOAc |
| 4b | Br | H | H | Br | HCl |
| 5a | Br | H* | Br* | Br | HOAc |
| 6a | Br | Br | Br | Br | HOAc |

*The substituents may be interchanged.

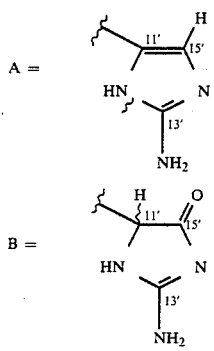

CHART B

General Procedure for the Solvent Partitioning of Samples 30-VI-81-1-2 and AHCE 631

```
30-VI-81-1-2
or
AHCE 631
```
(1) Homogenize with MeOH—$C_7H_8$ (3:1)
    (10 mL solvent/g wet weight sponge)
(2) Filter
(3) Add 1 liter $\underline{N}$ aq $NaNO_3$
    (10 mL/g wet weight sponge)
(4) Remove $C_7H_8$ layer and wash
    aqueous layer with additional $C_7H_8$ → $C_7H_8$ (dark orange)
→ $H_2O$ Wash with $CHCl_3$ (2×)

→ $CHCl_3$ (virtually no residue when dried)
→ $H_2O$

Wash with EtOAc (2×)

CHART B-continued

General Procedure for the Solvent Partitioning of Samples 30-VI-81-1-2 and AHCE 631

EtOAc ← | → $H_2O$
(1) Saturate with NaCl
(2) Wash with 1-BuOH (3×)

Combined EtOAc and 1-BuOH Layers (antibacterial and antiviral) ← 1-BuOH | $H_2O$ (1) CCD (2) HPLC → Purified Compounds

CHART C

Procedure for the Solvent Partitioning of 2-VII-81-1-1

```
2-VII-81-1-1
(1040 g)
```
(1) Homogenize with MeOH (4 × 2 L); filter
(2) Evaporate to dryness (Resulting solids (D1A) gave FABMS ions at m/z of 619(2Br):541(1Br) in a 7:1 ratio.)

(3) Triturate, filter, and wash, all with MeOH (1 L)

→ Solids (D1B)

(4) Evaporate to dryness
(5) Wash with acetone (2 × 125 mL) at 40° C.
(6) Filter off and retain solids → Acetone Solubles (D1C)

(7) Triturate retained solids with MeOH (3 × 175 mL) at 40° C., filter

→ MeOH Insolubles (D1D)
→ MeOH Solubles 35.7 g (D1E)

(1) Countercurrent Distribution
(2) HPLC

→ Purified Compounds

TABLE I

CCD Fractions - "A4B" Series:
Pooled Countercurrent Distribution Fractions Obtained By Partitioning Sample A4B

| Fraction Designation A4B- | CCD Tube Numbers | Weight (mg) | Tube Contents (by FABMS: m/z values and relative intensities) |
|---|---|---|---|
| A | 0–70 | | |
| B | 71–99 | | no brominated compounds |
| C | 100–113 | 71 | no brominated compounds |
| D | 115–135 | 138 | 782(2Br) |
| E | 136–155 | | no brominated compounds |
| F | 156–173 | | |
| G | 175–190 | 73 | 557(1Br) |
| H | 192–195 | 17 | 541(1Br):557(1Br):2:1 |

TABLE I-continued

CCD Fractions - "A4B" Series:
Pooled Countercurrent Distribution Fractions Obtained
By Partitioning Sample A4B

| Fraction Designation A4B- | CCD Tube Numbers | Weight (mg) | Tube Contents (by FABMS: m/z values and relative intensities) |
|---|---|---|---|
| I | 197–205 | 64 | 541(1Br):557(1Br):10:1 |
| J | 207–213 | 83 | 541(1Br) |
| K | 214–220 | 42 | 541(1Br) |
| L | 222–250 | 379 | 635(2Br):619(2Br):4:1 |
| M | 251–265 | 950 | 619(2Br) |
| N | 267–279, 291–295 | 1656 | 619(2Br) |
| P | 280–290 | 1048 | 619(2Br) |
| R | 297–312 | 406 | 619(2Br):697(3Br):5:4 |
| S | 314–341 | 327 | 775(4Br):697(3Br):10:3 |
| T | 342–397 | | |

TABLE II

CCD Fractions - "C" Series:
Pooled Countercurrent Distribution Fractions Obtained
By Partitioning Sample C1F

| Fraction Designation C1F- | CCD Tube Numbers | Weight (mg) | Tube Contents (by FABMS: m/z values and relative intensities) |
|---|---|---|---|
| A | 0–99 | 7480 | |
| B | 100–119 | 199 | |
| C | 120–139 | 165 | |
| D | 140–159 | 109 | |
| E | 160–179 | 77 | |
| F | 180–195 | 77 | no brominated compounds |
| G | 196–229 | 459 | 635(2Br):594(2Br):100:3 |
| H | 231–239 | 254 | 635(2Br):619(2Br):10:3 |
| I | 240–249 | 425 | 635(2Br):619(2Br):1:1 |
| J | 250–259 | 604 | 619(2Br):635(2Br):5:2 |
| K | 261–265 | 265 | 619(2Br) |
| L | 266–269 | 154 | 619(2Br):697(3Br):1:1 |
| M | 271–272 | 53 | 697(3Br):619(2Br):5:2 |
| N | 273–277 | 109 | 697(3Br) |
| O | 278–279 | 35 | 697(3Br):775(4Br):10:1 |
| P | 280–289 | 140 | 697(3Br):775(4Br):1:1 |
| Q | 291–320 | 250 | 775(4Br):742(3Br):697(3Br) 10:3:1 |
| R | 321–340 | 129 | no brominated compounds |
| S | 341–400 | 628 | |

TABLE III

CCD Fractions - "D" Series:
Pooled Countercurrent Distribution Fractions Obtained
By Partitioning Sample D1E

| Fraction Designation D1E- | CCD Tube Numbers | Weight (mg) | Tube Contents (by FABMS: m/z values and relative intensities) |
|---|---|---|---|
| A | 0–200 | 22520 | |
| B | 200–300 | 3300 | |
| C | 300–370 | 1350 | |
| D | 371–400 Fraction Collector Tube Numbers | 180 | no brominated compounds |
| E | 318–281 | 269 | some 557(1Br) |
| F | 280–261 | 167 | 541(1Br):557(1Br):1:1 |
| G | 260–213 | 566 | 541(1Br) |
| H | 212–196 | 171 | 566(2Br):541(1Br):3:1 |
| I | 195–167 | 677 | 635(2Br) |
| J | 166–151 | 841 | 635(2Br):619(2Br):10:1 |
| K | 150–130 | 2144 | 619(2Br):635(2Br) mixture |
| L | 129–124 | 858 | 619(2Br):635(2Br) mixture |
| M | 123–118 | 957 | 619(2Br):635(2Br) mixture |
| N | 117–113 | 918 | 619(2Br):635(2Br) mixture |
| O | 112–107 | 926 | 619(2Br):635(2Br) mixture |
| P | 106–97 | 573 | 619(2Br) |
| Q | 96–77 | 1135 | some 697(3Br) |
| R | 76–71 | 280 | 697(3Br) |
| S | 70–66 | 171 | 697(3Br):775(4Br):742(2Br) 20:12:1 |

TABLE III-continued

CCD Fractions - "D" Series:
Pooled Countercurrent Distribution Fractions Obtained
By Partitioning Sample D1E

| Fraction Designation D1E- | CCD Tube Numbers | Weight (mg) | Tube Contents (by FABMS: m/z values and relative intensities) |
|---|---|---|---|
| T | 65–61 | 189 | 775(4Br):697(3Br):5:2 |
| U | 60–56 | 200 | 775(4Br):697(3Br):10:1 |
| W | 55–31 | 1010 | 775(4Br) |
| X | 30–0 | | |

TABLE IV

Antimicrobial Activities for 1a–8a[a]

| Compound | 100 μg/disk | 50 μg/disk | 10 μg/disk |
|---|---|---|---|
| *Escherichia coli* | | | |
| 1a | 11 | 8 | 0 |
| 2a | 11 | 10 | 7 |
| 3a | 7 | 7 | 0 |
| 4a | 9 | 9 | 7 |
| 5a | 8 | 8 | 7 |
| 6a | 7 | 7 | 0 |
| 7a | 0 | 0 | 0 |
| 8a | 10 | 8 | 0 |
| *Bacillus subtilis* | | | |
| 1a | 12 | 11 | 7 |
| 2a | 17 | 16 | 9 |
| 3a | 10 | 10 | 0 |
| 4a | 16 | 15 | 10 |
| 5a | 12 | 12 | 10 |
| 6a | 9 | 9 | 8 |
| 7a | 8 | 7 | 0 |
| 8a | 15 | 14 | 0 |

[a]All compounds inactive against *Saccharomyces cerevisiae* and *Penicillium atrovenetum* at 100 μg per disc. All values are reported as the diameter (in mm) of the clear zone of inhibition using a disc diffusion type assay, and are averages of at least two determinations.

TABLE V

Antiviral Activities for 1a–8a[a]

| Compound | 200 μg/disk | 100 μg/disk | 50 μg/disk | 20 μg/disk |
|---|---|---|---|---|
| Herpes Simplex Virus type 1 (HSV-1) | | | | |
| 1a | +++ 18 | ++ 15 | ++ 12 | ++ 11 |
| 2a | +++ 21 | ++ 13 | ++ 13 | ++ 11 |
| 3a | ++ 14 | ++ 12 | ++ 11 | + 9 |
| 4a | +++ 17 | ++ 14 | ++ 13 | + 10 |
| 5a | ++ 13 | ++ 11 | ++ 11 | + 9 |
| 6a | ++ 12 | ++ 11 | ++ 11 | + 9 |
| 7a | + [b] | − 0 | − 0 | − 0 |
| 8a | ++ 12[b] | ++ 11[b] | + [b] | − 0 |
| Vesicular Stomatitus Virus (VSV) | | | | |
| 1a | + 8 | ± 7 | − 0 | − 0 |
| 2a | ++ 13 | ++ 11 | + 8 | ± 7 |
| 3a | ++ 12 | + 10 | n.d. [c] | − 0 |
| 4a | ++ 12 | + 10 | + 8 | − 0 |
| 5a | + 10 | + 10 | − 0 | − 0 |
| 6a | + 10 | + 9 | + 8 | − 0 |
| 7a | − 0 | n.d. [c] | n.d. [c] | n.d. [c] |
| 8a | + [b] | + 8 | − 0 | − 0 |

[a]Assays performed using 6.5 mm disks. No cytotoxicity was observed for any compounds with the exception of traces of cytotoxicity (zones ≦8 mm) found for all concentrations of 6a and the 200 μg/disk sample of 7a. Antiviral activities are reported using two scales: the ++ system/the zone diameter (in mm) system. Activities were measured by zones of inhibition (in mm) and converted for this table using the scale: ≧16 mm = +++; 11-15 mm = ++; 8-10 mm= +; 7 mm = ±; and ≦7 = −. All values are averages of two or more determinations with the exception of values for 3a and 7a.
[b]Diffuse antiviral activity manifested by fewer and smaller viral plaques in a diffuse zone radiating out from the sample disk.
[c]n.d = not determined.

TABLE VI

Antiviral and Cytotoxicity Activities for 1a-8a
Determined by Dr. R. G. Hughes, Jr.[a]
Cytotoxicity to Monkey Kidney Cells (CV-1)
(Herpes Simplex Virus type 1 (HSV-1))

| Compound | 100 μg/disk | 50 μg/disk | 25 μg/disk |
|---|---|---|---|
| 1a | 5 (±) | 5 (±) | 5 (±) |
| 2a | 7 (++) | 5 (+++) | 5 (−) |
| 3a | 7 (+++) | 5 (++) | 5 (−) |
| 4a | 8 (++) | 5 (+) | 5 (−) |
| 5a | 7 (++) | 5 (±) | 5 (−) |
| 6a | 10 (±) | 8 (±) | 6 (−) |
| 7a | 6 (−) | 5 (−) | 5 (−) |
| 8a | 6 (+) | 5 (−) | 5 (−) |

[a]Cytotoxicity is reported as zone diameters (in mm). Cytotoxicity values of 8 or less essentially indicate noncytotoxicity (disk diameter = 6.5 mm).
HSV-1 activity reported as +++ (strong), ++ (moderate), + (light), ± (questionable), and − (negative). All doses were inactive against vesicular stomatitis virus (VSV) with the possible exception of 7a which gave a value of ± at 100 μg/disk.

TABLE VII

Biochemical Prophage Induction Assay for 1a-8a[a]

| Compound | 100 μg/disk | 20 μg/disk | 10 μg/disk |
|---|---|---|---|
| 1a | +++/10 | ++/7 | ++/6 |
| 2a | +++/9 | n.d.[b] | ++/6 |
| 3a | n.d. | +/3 | +/2 |
| 4a | +/5-grey | +/3-grey | ±/2-grey |
| 5a | +/3-grey | ±/2-grey | ±/2-grey |
| 6a | ±/2-grey | ±/2-grey | ±/2-grey |
| 7a | +/4 | n.d. | +/4 |
| 8a | +++/9 | n.d. | ++/6 |

[a]Tested with the disc diffusion method instead of the direct spotting technique. Activity is reported using two color intensity scales: a numerical scale ranging from 0 (no color under the disc) to 10 (a very strong red color diffusing for some distance away from the disc location), and the ++ scale. The conversion is: 8–10 = +++, 6–7 = ++, 3–5 = +, 1–2 = ±, and 0 = −. Results for 10 μg discs were the same on both LBE and LBE$_{amp}$ plates. Compounds 7a and 8a typically gave more diffuse zones than compounds 1a–6a, presumably due to water solubility. Compounds 4a–6a typically gave grey zones instead of red. All values are averages of at least two determinations.
[b]n.d. = not determined.

We claim:

1. A compound selected from the group consisting of a compound of the following formula

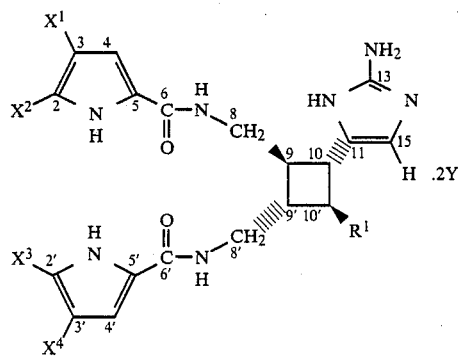

wherein R' is B where

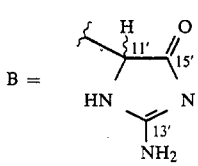

B = and wherein (1) $X^1$ is Br; $X^2$, $X^3$, and $X^4$ are H; R' is B, and Y is HOAC;
(2) $X^1$ is Br; $X^2$ and $X^3$ are H; $X^4$ is Br; R' is B; and Y is HOAC; and,
(3) $X^1$ is Br; $X^2$ and $X^3$ are H; $X^4$ is Br; R' is B; and Y is HCl.

2. A compound according to claim 1 wherein $X^1$ is Br; $X^2$, $X^3$, and $X^4$ are H; $R^1$ is B, and Y is HOAc.

3. A compound according to claim 1 wherein $X^1$ is Br, $X^2$ and $X^3$ are H; $X^4$ is Br; $R^1$ is B; and Y is HOAc.

4. A compound according to claim 1 wherein $X^1$ is Br; $X^2$ and $X^3$ are H; $X^4$ is Br; $R^1$ is B; and Y is HCl.

5. A compound of the following formula:

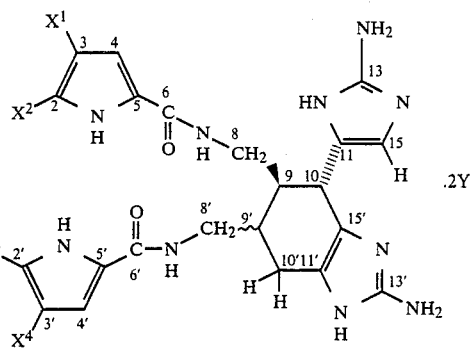

wherein $X^1$, $X^2$, $X^3$, and $X^4$ are selected from Br, Cl, I, or H; and Y is an acid addition salt; or the free base; or an acylate thereof.

6. A compound according to claim 5 wherein $X^1$ is Br, $X^2$ and $X^3$ are H; $X^4$ is Br; and Y is HOAc.

7. A compound according to claim 5 wherein $X^1$ is Br, $X^2$ and $X^3$ are H; $X^4$ is Br: and Y is HCl.

8. A compound according to claim 5 wherein $X^1$ is Br, $X^2$ is H, $X^3$ and $X^4$ are Br, and Y is HOAc.

9. A compound according to claim 5 wherein $X^1$, $X^2$, $X^3$, and $X^4$ are Br; and Y is HOAc.

10. A process for treating humans or animals infected with herpes simplex virus type I or vesicular stomatitis virus which comprises administering, to a human or animal in need of treatment, an effective antiviral amount of a compound with the following formula:

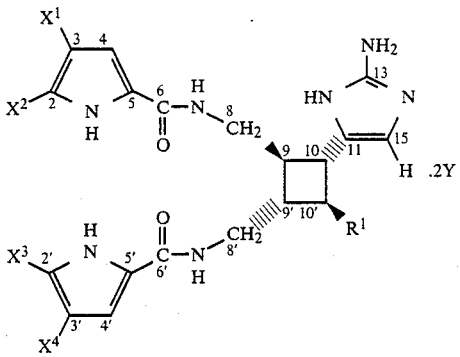

wherein $X^1$, $X^2$, $X^3$, and $X^4$ are selected from Br, Cl, I, or H; $R^1$ is either A or B where:

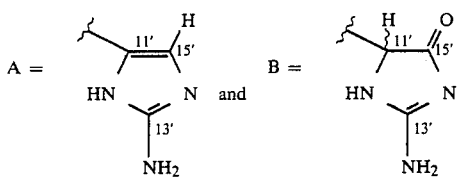 and and Y is an acid addition salt; or the free base; or an acylate thereof.

11. A process according to claim 10 wherein $X^1$ is Br; $X^2$, $X^3$, and $X^4$ are H; $R^1$ is A; and Y is HOAc.

12. A process according to claim 10 wherein $X^1$ is Br, $X^2$ and $X^3$ are H; $X^4$ is Br; $R^1$ is A; and Y is HOAc.

13. A process according to claim 10 wherein $X^1$ is Br, $X^2$ and $X^3$ are H, $X^4$ is Br, $R^1$ is A, and Y is HCl.

14. A process according to claim 12 wherein $X^1$, $X^2$, $X^3$, and $X^4$ are Br; $R^1$ is A; and Y is HOAc.

15. A process according to claim 12 wherein $X^1$ is Br; $X^2$, $X^3$, and $X^4$ are H; $R^1$ is B; and Y is HOAc.

16. A process according to claim 12 wherein $X^1$ is Br, $X^2$ and $X^3$ are H, $X^4$ is Br, $R^1$ is B, and Y is HOAc.

17. A process according to claim 10 wherein $X^1$ is Br, $X^2$ and $X^3$ are H, $X^4$ is Br, $R^1$ is B, and Y is HCl.

18. A process for treating humans or animals infected with herpes simplex virus type I or vesicular stomatitis virus which comprises administering, to a human or animal in need of treatment, an effective antiviral amount of a compound with the following formula:

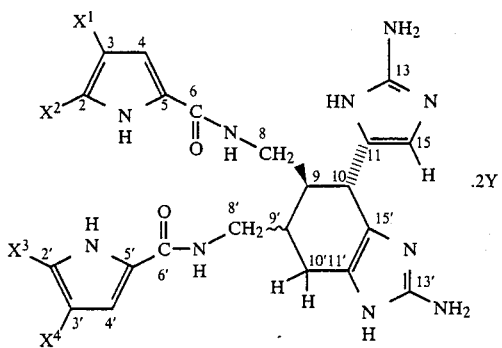

wherein $X^1$, $X^2$, $X^3$, and $X^4$ are selected from Br, Cl, I, or H; and Y is an acid addition salt; or the free base; or an acylate thereof.

19. A process according to claim 18 wherein $X^1$ is Br, $X^2$ and $X^3$ are H, $X^4$ is Br, and Y is HOAc.

20. A process according to claim 18 wherein $X^1$ is Br, $X^2$ and $X^3$ are H, $X^4$ is Br, and Y is HCl.

21. A process according to claim 18 wherein $X^1$ is Br, $X^2$ is H, $X^3$ and $X^4$ are Br, and Y is HOAc.

22. A process according to claim 18 wherein $X^1$, $X^2$, $X^3$, and $X^4$ are Br, and Y is HOAc.

23. A process for treating humans or animals infected with a susceptible gram positive or gram negative microbe which comprises administering to a human or animal in need of such treatment an effective antimicrobial amount of a compound selected from the group consisting of a compound with the following formula:

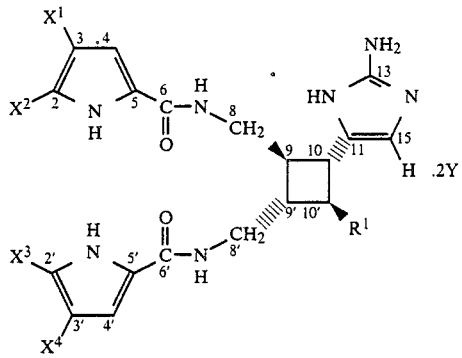

wherein R' is B where

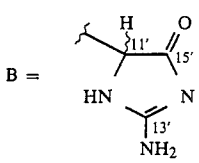

and wherein
(1) $X^1$ is Br; $X^2$, $X^3$, and $X^4$ are H; R' is B, and Y is HOAC;
(2) $X^1$ is Br; $X^2$ and $X^3$ are H; $X^4$ is Br; R' is B; and Y is HOAC; and,
(3) $X^1$ is Br; $X^2$ and $X^3$ are H; $X^4$ is Br; R' is B; and Y is HCl.

24. A process according to claim 23 wherein $X^1$ is Br; $X^2$, $X^3$, and $X^4$ are H; $R^1$ is B, and Y is HOAc.

25. A process according to claim 23 wherein $X^1$ is Br, $X^2$ and $X^3$ are H; $X^4$ is Br; $R^1$ is B; and Y is HOAc.

26. A process according to claim 23 wherein $X^1$ is Br; $X^2$ and $X^3$ are H; $X^4$ is Br; $R^1$ is B; and Y is HCl.

27. A process for treating humans or animals infected with a susceptible gram positive or gram negative microbe which comprises administering to a human or animal in need of such treatment an effective antimicrobial amount of a compound with the following formula:

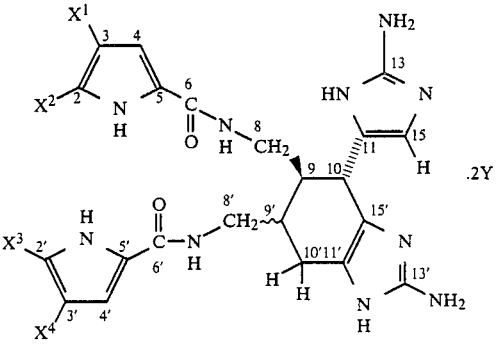

wherein $X^1$, $X^2$, $X^3$, and $X^4$ are selected from Br, Cl, I, or H; and Y is an acid addition salt; or the free base; or an acylate thereof.

28. A process according to claim 27 wherein $X^1$ is Br, $X^2$ and $X^3$ are H, $X^4$ is Br, and Y is HOAc.

29. A process according to claim 27 wherein $X^1$ is Br, $X^2$ and $X^3$ are H, $X^4$ is Br, and Y is HCl.

30. A process according to claim 27 wherein $X^1$ is Br, $X^2$ is H, $X^3$ and $X^4$ are Br, and Y is HOAc.

31. A process according to claim 27 wherein $X^1$, $X^2$, $X^3$, and $X^4$ are Br, and Y is HOAc.

* * * * *

UNITED STATES PATENT AND TRADEMARK OFFICE
CERTIFICATE OF CORRECTION

PATENT NO. : 4,737,510

DATED : April 12, 1988

INVENTOR(S) : Kenneth Rinehart, Jr.

It is certified that error appears in the above-identified patent and that said Letters Patent are hereby corrected as shown below:

Column 3: line 5: "Agelas" should read --*Agelas*--; line 6: "Agelas coniferin" should read --*Agelas coniferin*--.

Column 5: line 19: after "*Saccharomyces*" delete ","; line 43: "Agelas" should read --*Agelas*--; line 43: "Agelas" should read --*Agelas*--.

Column 6: line 39: after "5μm" insert -- - --; line 47: "B" should read --β--.

Column 7: line 28: "43:28192830" should read --43:2819-2830--; line 49: "%1" should read --μl--.

Column 10: line 22: after "600" delete "-".

Column 11: line 16: "(∈ y27 300)" should read --(∈ 27 300)--; line 60: "Amal." should read --Anal.--.

Column 15: line 40: "dicalcius" should read --dicalcium--.

Claim 14: line 1: "12" should read --10--.

Claim 15: line 1: "12" should read --10--.

Claim 16: line 1: "12" should read --10--.

Signed and Sealed this

Thirteenth Day of September, 1988

Attest:

DONALD J. QUIGG

Attesting Officer     Commissioner of Patents and Trademarks

UNITED STATES PATENT AND TRADEMARK OFFICE
CERTIFICATE OF CORRECTION

PATENT NO. : 4,737,510
DATED : April 12, 1988
INVENTOR(S) : Kenneth L. Rinehart, Jr.

It is certified that error appears in the above-identified patent and that said Letters Patent is hereby corrected as shown below:

Column 1, following the title of the invention insert --This invention was made with government support under grants PCM77-12584 and PCM81-21494 awarded by the National Science Foundation, and AI 04769 and GM 27029 awarded by the National institutes of Health. The government has certain rights in this invention.--

Signed and Sealed this

Fifteenth Day of August, 1989

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO. : 4,737,510
DATED : April 12, 1988
INVENTOR(S) : Rinehart, Jr.

It is certified that error appears in the above-indentified patent and that said Letters Patent is hereby corrected as shown below:

Column 1, line 1,

"This invention was made with Government support under Grant No. AI04769 and GM 27029 awarded by the National Institutes of Health. The Government has certain rights in the invention."

Signed and Sealed this

Fourth Day of April, 1995

*Attest:*

BRUCE LEHMAN

*Attesting Officer*  *Commissioner of Patents and Trademarks*